United States Patent [19]

Holmes

[11] 4,328,794
[45] May 11, 1982

[54] TRACTION SPLINT

[76] Inventor: Robert E. Holmes, 7600 Mine Valley Dr., Raleigh, N.C. 27609

[21] Appl. No.: 139,451

[22] Filed: Apr. 11, 1980

[51] Int. Cl.³ .............................................. A61F 5/04
[52] U.S. Cl. ..................................................... 128/85
[58] Field of Search .................. 128/85, 86, 75, 84 R, 128/84 C; 242/107.5

[56] References Cited

U.S. PATENT DOCUMENTS 3,065,925 11/1962 Appleton ........................... 242/107.5
3,151,823 10/1964 Clarke ............................... 242/107.5
3,419,002 12/1968 Santosus ................................ 128/85
3,477,428 11/1969 Hare ...................................... 128/85

Primary Examiner—John D. Yasko
Attorney, Agent, or Firm—John G. Mills, III; Paul Bogdon

[57] ABSTRACT

This invention is a traction splint including a tension applying mechanism with an outer knob to apply tension to a tension stirrup through belting wound about a shaft while such tension is released by turning of an inner knob in the opposite direction. Both of these knobs are uni-directional relative to rotative movement but in opposite directions. A folding support leg and relatively simple and yet extremely efficient bindings and appendage supports are also included features.

5 Claims, 4 Drawing Figures

TRACTION SPLINT

FIELD OF INVENTION

This invention relates to medical appliances and more particularly to splints which allow traction to be applied to an injured appendage.

BACKGROUND OF INVENTION

Since man first began to doctor himself, splints have been used on injured appendages to maintain alignment of bones which are fractured or broken. In recent times portable or emergency splints have been developed, some of which have included means for applying traction to the appendage. These traction means have generally included ratchet type mechanisms which allow tightening in predefined increments with no adjustment being possible between such increments. Also the release mechanisms have been difficult to manipulate, particularly in adverse conditions such as when the hands of the user are wet or cold or both. Additionally, to release a ratchet device, further tightening of the same is required to take the pressure off the pall. Other attempts at applying tension to splint type devices have been made but these likewise have similar shortcomings.

SUMMARY OF INVENTION

After much research and study into the abovementioned problems, the present invention has been developed to provide a traction splint which allows tension to be applied in smooth, infinitely small increments and yet the same can as readily be released in smooth rotative fashion. No ratchets or similar mechanisms are involved thus by the manipulation of adjacent uni-directional knobs, both tightening and release of tension can be smoothly accomplished.

The above, coupled with a strong, lightweight frame with a folding support leg and modern appendage engaging straps allow the present invention to be quickly placed in use and as quickly removed from the patient when desired.

In view of the above, it is an object of the present invention to provide a tension type splint with an improved tension applying mechanism.

Another object of the present invention is to provide a tension mechanism for a traction splint which can be adjusted in infinitely minute increments.

Another object of the present invention is to provide a smooth operating tension mechanism for a traction splint which can be tightened smoothly in one direction by manipulating a single knob and released in the opposite direction by manipulating a second knob.

Another object of the present invention is to provide an improved support leg for a traction type splint.

Another object of the present invention is to provide a lightweight, smooth operating traction splint for use by emergency medical personnel as well as others in the medical field.

Other objects and advantages of the present invention will become apparent and obvious from a study of the following description of the accompanying drawings which are merely illustrative of such invention.

DETAILED DESCRIPTION OF INVENTION

Figure 1:
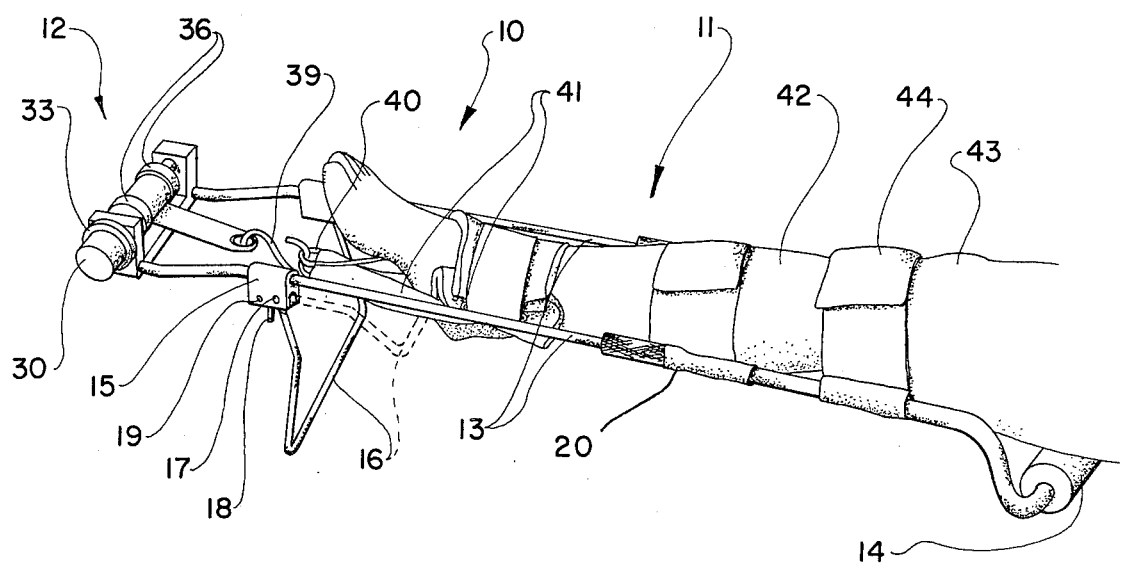
FIG. 1 is a perspective view of the tension splint of the present invention disposed in the use mode.

With further reference to the drawings, the tension splint of the present invention, indicated generally at 10, includes an appendage support frame, indicated generally at 11, and a traction applying mechanism, indicated generally at 12. The support frame 11 includes parallely disposed side members 13 with a somewhat U-shaped portion 14 joining adjacent ends of such side members. Adjacent each of the opposite ends of the side members is a lockable release mechanism indicated at 15. This mechanism pivotably mounts generally U-shaped support leg 16 on pins 17. A release finger 18 is provided and is pivotably mounted within mechanism 15 on pin 19. Since the operation of finger released, quick lock mechanisms are well known to those skilled in the art, further detailed discussion of this portion of the invention is not deemed necessary.

Suffice it to say that support leg 16 pivots back to the position shown in dotted lines in FIG. 1 when not in use and is locked in the position shown in solid lines in FIG. 1 when in use or when so desired. Also the locking mechanism need only be provided on one side with the other side being simply pivotably mounted.

A plurality of appendage support means 20 are secured between side members 13. These appendage support means are preferably constructed from a webbing type material for comfort and self-contouring purposes.

Figure 2:
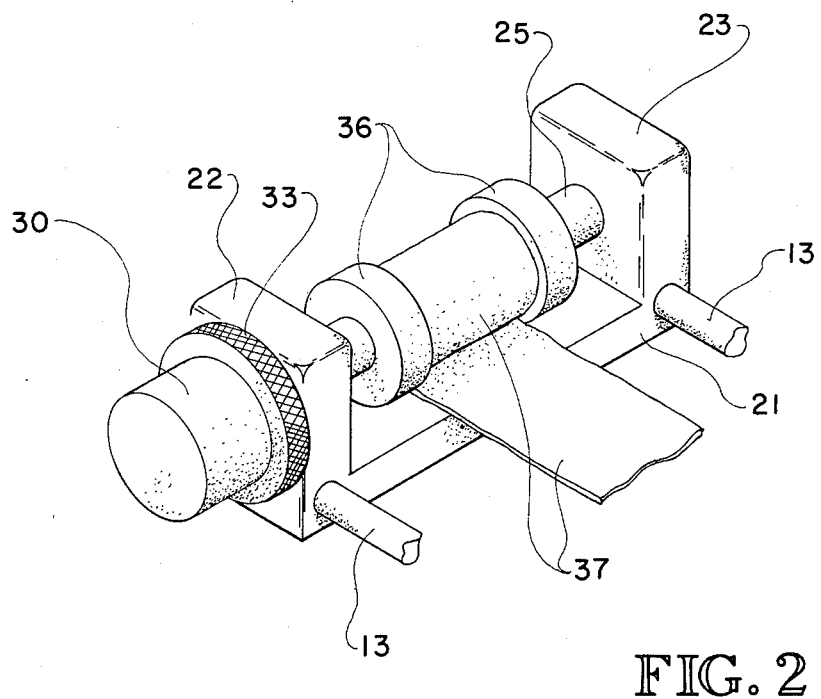
FIG. 2 is a fragmentary view of the tension take-up portion of the present invention.
Figure 3:
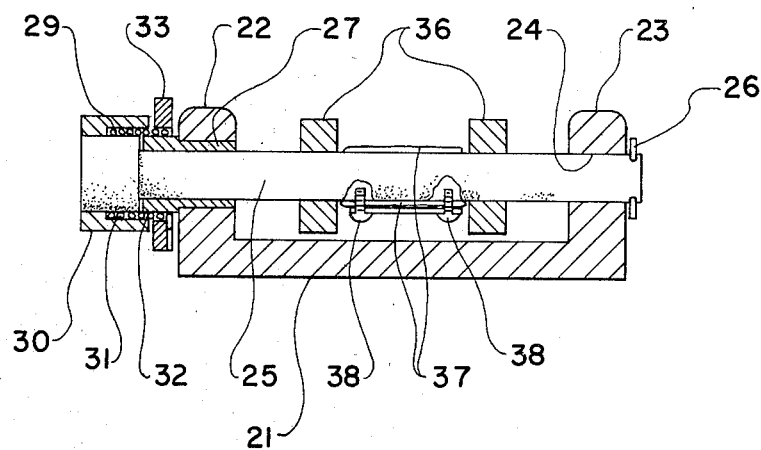
FIG. 3 is a sectional view taken through lines 3—3 of FIG. 2.

The ends of side members 13 opposite U-shaped portion 14 terminates in at a generally U-shaped block 21 as can clearly be seen in FIG. 2. Block 21 includes a pair of flanges 22 and 23 at opposite ends thereof. An opening 24 is provided in flange 23 and is adapted to rotatively receive shaft 25. A retaining means such as clip ring 26 is provided on one end of shaft 25 as can clearly be seen in FIG. 3.

Figure 4:
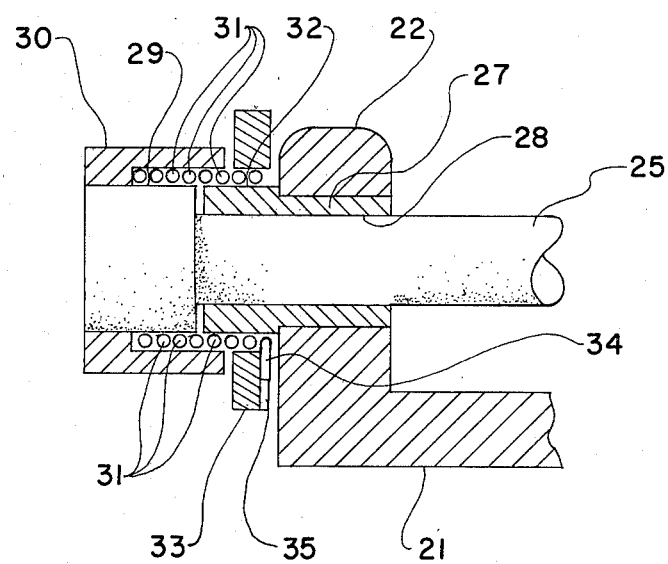
FIG. 4 is an enlarged sectional view of the tension locking and release portion of the present invention.

Flange 22 has an opening therein which is adapted to bindingly receive bushing 27. This bushing includes an axial opening 28 which is adapted to rotatively receive shaft 25. The end of shaft 25 opposite retaining ring 26 has an enlarged or shoulder portion 29 thereon as can clearly be seen in FIGS. 3 and 4. A knob-like housing 30 is fixedly secured to the outer portion of shoulder 29 thus forming a circular, slot-like opening 31 between the shoulder and the housing which is adapted to receive coil spring 31 as clearly shown in FIG. 4.

Bushing 27 includes a generally circular shoulder portion 32. This shoulder is disposed adjacent to shoulder 29 and is of the same basic size and configuration again as can clearly be seen in the sectional views.

A release ring 33 is mounted over coil spring 31 between knob housing 30 and the outer portion of flange 22. The inner end of spring 31 has an outwardly projecting portion or ear 34 formed thereon. This ear is adapted to retainingly engage a slot 35 formed on the inner surface of release ring 33.

Thus it can be seen that as knob 30 is turned in the direction of the coils of spring 31, it can freely rotate without binding thus rotating shaft 25 therewith. When knob 30 is attempted to be turned in the opposite direction, however, the coil spring 31 will bind between shaft shoulder 29 and bushing shoulder 32 to prevent rotation in such direction. To release this binding pressure to rotate shaft 25 in the direction it is locked against, release ring 33 is turned in such direction thus the ear 34 of spring 31 will be moved, rotating in turn shaft 25 and its related knob 30.

In summary, knob 30 can rotate shaft 25 in one direction only and release ring 33 can rotate shaft 25 in the opposite direction only thus complete control of movement of the shaft 35 is accomplished.

A pair of guides 36 are provided on shaft 25 intermediate flanges 22 and 23. Between these guides is secured a flexible web or belt 37 which can be fixed to shaft 25 by means such as screws 38. A hook means 39 is mounted on the end of belt 37 opposite shaft 25.

The end of hook means 39 opposite its connection to belt 37 is adapted to engage pull rings 40 of web tension stirrup 41. Since the use of stirrups of this type are well known to those skilled in the art, further detailed description of the mounting of the same on the appendage of the patient is not deemed necessary.

To use the traction splint 10 of the present invention, the side members 13 are placed on either side of the appendage 42 of the patient 43 so that such appendage rests on appendage support means 20. Splint-to-appendage bindings 42 having velcro on other suitable securing means thereon are connected about the appendage as shown in FIG. 1. The tension stirrup 41 is then secured about the end of the appendage such as about the ankle of the patient 43 as shown in FIG. 1.

Belt 37 is then unwound from shaft 25 by turning release ring 33 until hook means 39 can be connected to tension rings 40 of stirrup 41. Knob 30 is then turned in a winding direction, this being the only direction in which it will turn. Belt 37 is thus wound about shaft 25 until the desired tension is placed on tension stirrup 41.

If it is desired to support the splint 10 of the present invention off the ground, support leg 16 can be moved into the position shown in solid lines in FIG. 1.

To release the tension on the appendage, release ring 33 is simply rotated in the only direction in which it will turn, namely, the unwinding direction for belt 37, thus releasing tension on stirrup 41. Also whenever support leg 16 is no longer needed, release finger 18 can be manipulated to allow such leg to pivot back against side members 13 of splint 10 as indicated by dotted lines in FIG. 1.

From the above, it can be seen that the present invention provides a tension splint which is simple and easy to use, provides infinite adjustment of the tension belt, and is simple to release while at the same time being so constructed that the danger of accidental release is for all practical purposes eliminated. Also, the present invention is relatively inexpensive to manufacture and yet is highly efficient in accomplishing its intended use purpose.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended Claims are intended to be embraced therein.

What is claimed is:

1. An improved traction splint type device comprising: a pair of elongated, generally parallely disposed side members; means connecting said members adjacent one end thereof; a traction mechanism support means secured to and extending between said members adjacent their ends opposite said connecting means; a traction belt pick-up shaft rotatively mounted on said support means adjacent one of said side means; a bushing means fixedly mounted on said support means adjacent said other side means and rotatively mounting said shaft, said bushing outwardly projecting on one side of said support means; a shoulder means fixedly secured to the end of said shaft and being disposed adjacent said bushing; a coil spring means wound about said bushing and said shoulder; a housing knob covering at least a portion of said shoulder and its adjacent spring; a release means connected to one end of said spring and rotatively mounted between said housing and said support whereby said housing can be rotated in one direction only to rotate said shaft in that direction while said ring can rotate in the opposite direction only to rotate said shaft in that direction; and belt means secured at one end to said shaft and at its other end to an appendage requiring traction whereby an improved traction splint is provided.

2. The splint of claim 1 whereby a ground support means is provided on said side members adjacent said appendage mechanism support means.

3. The splint means of claim 2 wherein said ground support means is pivotable to a folded, out of use position.

4. The splint of claim 3 wherein a means for locking said ground support in ground engaging position is provided.

5. The splint of claim 1 wherein an appendage encircling stirrup is connected to the end of said belt opposite said shaft.

* * * * *